(12) United States Patent
Knodel

(10) Patent No.: US 7,678,121 B1
(45) Date of Patent: *Mar. 16, 2010

(54) SURGICAL STAPLING TOOL

(75) Inventor: Bryan D. Knodel, Flagstaff, AZ (US)

(73) Assignee: Cardica, Inc., Redwood City, CA (US)

( * ) Notice: Subject to any disclaimer, the term of this patent is extended or adjusted under 35 U.S.C. 154(b) by 1273 days.

This patent is subject to a terminal disclaimer.

(21) Appl. No.: 11/158,413

(22) Filed: Jun. 22, 2005

Related U.S. Application Data

(63) Continuation-in-part of application No. 11/022,551, filed on Dec. 23, 2004, now Pat. No. 7,462,185.

(51) Int. Cl.
*A61B 17/10* (2006.01)

(52) U.S. Cl. .................................. 606/139; 227/175.1

(58) Field of Classification Search ................. 606/139, 606/143, 219, 142; 227/175.1, 176.1–179.1
See application file for complete search history.

(56) References Cited

U.S. PATENT DOCUMENTS

| 4,396,139 | A | 8/1983 | Hall et al. | |
| 5,158,567 | A | 10/1992 | Green | |
| 5,792,094 | A | 8/1998 | Stevens et al. | |
| 5,861,005 | A | 1/1999 | Kontos | |
| 5,972,023 | A | 10/1999 | Tanner et al. | |
| 6,149,660 | A * | 11/2000 | Laufer et al. | 606/143 |
| 6,352,541 | B1 * | 3/2002 | Kienzle et al. | 606/143 |
| 6,482,224 | B1 | 11/2002 | Michler et al. | |
| 7,462,185 | B1 * | 12/2008 | Knodel | 606/139 |
| 2005/0090834 | A1 | 4/2005 | Chiang et al. | |
| 2005/0090843 | A1 | 4/2005 | Bolduc | |
| 2005/0187613 | A1 | 8/2005 | Bolduc et al. | |

* cited by examiner

*Primary Examiner*—(Jackie) Tan-Uyen T. Ho
*Assistant Examiner*—Melanie Tyson
(74) *Attorney, Agent, or Firm*—Brian A. Schar

(57) ABSTRACT

A surgical stapler may include a catheter connected to a stapler head and a handle. The stapler head may be configured for introduction into the vasculature of a patient. The stapler head may include a driver movable in two dimensions relative to a plurality of staples. Each staple may be held by a holder, where the holders may be connected together or fabricated as a unitary cartridge.

6 Claims, 12 Drawing Sheets

SURGICAL STAPLING TOOL

This patent application is a continuation-in-part of U.S. patent application Ser. No. 11/022,551, filed on Dec. 23, 2004, now U.S. Pat. No. 7,462,185 which is hereby incorporated by reference in its entirety.

FIELD OF THE INVENTION

The present invention relates generally to medical devices, and more particularly to an intravascular stapler.

BACKGROUND

Abdominal aortic aneurysm (AAA) is an abnormal ballooning of the abdominal portion of the aorta, which is the major artery routing blood from the heart to all organs. Abdominal aortic aneurysm involves a dilation, stretching, or ballooning of the abdominal aorta, which is the section of the aorta residing in the abdominal cavity. Causes of abdominal aortic aneurysm include infection, tissue disease (such as atherosclerosis) resulting in weakening of the connective tissue component of the arterial wall, trauma, and Marfan's syndrome. Abdominal aortic aneurysm can affect anyone, but it is most often seen in men aged 40 to 70. Most commonly, abdominal aortic aneurysms occur in the portion of the vessel below the renal artery origins, and may extend into the vessels supplying the hips and pelvis.

A common complication of AAA is rupture. This is a medical emergency where the aneurysm breaks open, resulting in profuse bleeding. Aortic rupture is life-threatening; the likelihood of death after rupture is generally considered to be 80-90%. Once an aneurysm reaches 5 cm in diameter, it is usually considered necessary to treat it to prevent rupture.

Surgical repair or replacement of the section of aorta that includes the aneurysm is recommended for patients with symptoms and for patients with aneurysms greater than 5 cm in diameter, as they are at high risk of fatal rupture. Because surgery for abdominal aortic aneurysm is risky, the surgeon may wait for the aneurysm to expand to a size at which the risk of complications exceeds the risk of surgery. Below 5 cm, the risk of the aneurysm rupturing is lower than the risk of conventional surgery in patients with normal surgical risks. However, it is undesirable to wait for a known AAA to get worse in order to treat it.

Placement of an AAA graft is also a treatment option. An AAA graft is a tube or tubelike structure placed inside the aorta. Its placement can be performed without an abdominal incision, with specialized catheters that are introduced through arteries at the groin. However, not all patients with abdominal aortic aneurysms are candidates for grafts, however. Further, some AAA grafts in the past have had difficulties that have resulted in their removal from the marketplace, such as breakage of the hooks that hold the AAA graft in place in the aorta, and difficulties with the tools for deploying the AAA grafts.

BRIEF DESCRIPTION OF THE DRAWINGS

The use of the same reference symbols in different figures indicates similar or identical items.

DETAILED DESCRIPTION

Surgical Stapling Tool

Figure 1:
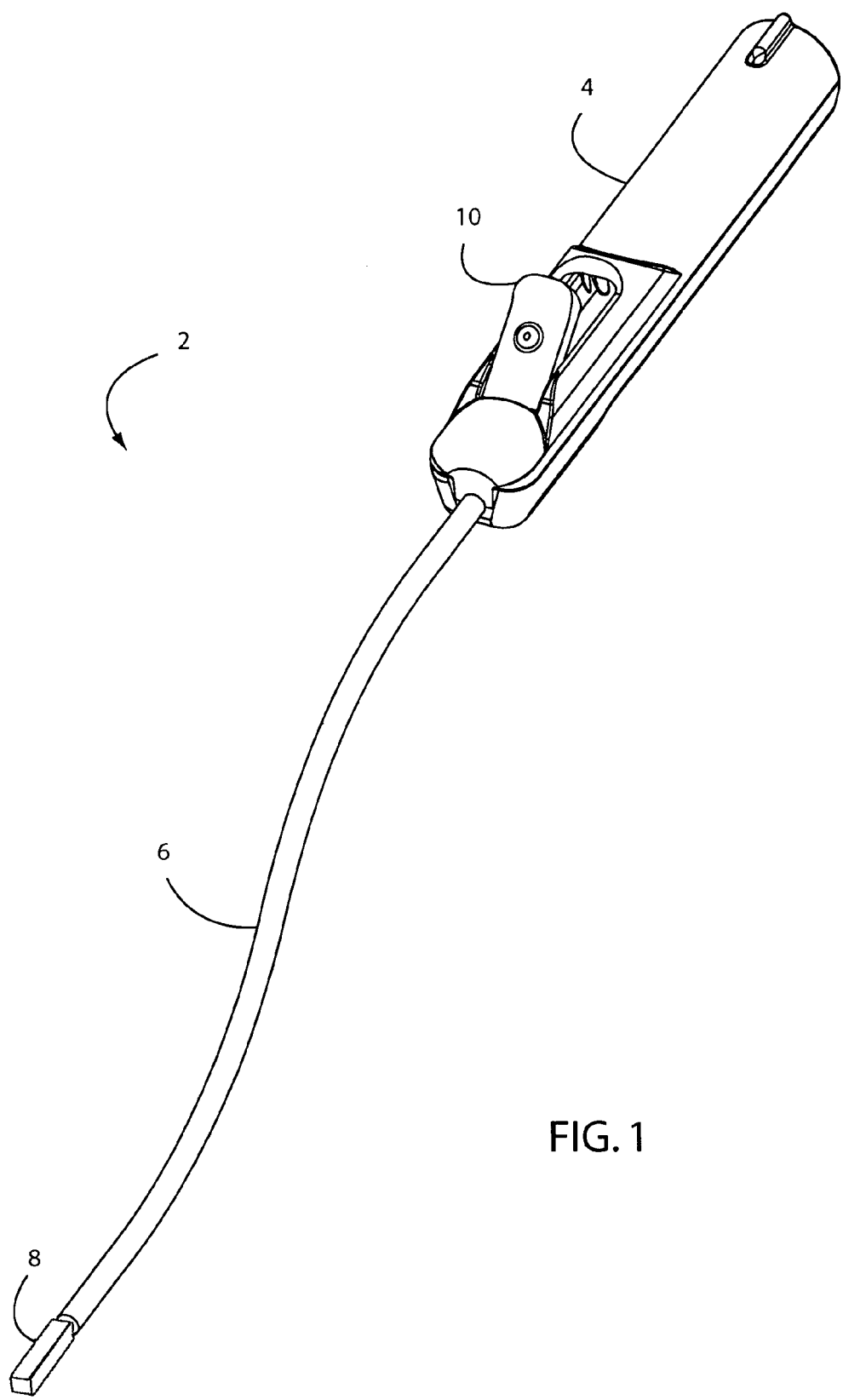
FIG. 1 is a perspective view of an surgical stapling tool having a stapler head connected to a handle by a catheter.

Referring to FIG. 1, an exemplary surgical stapling tool 2 is shown. The surgical stapling tool 2 includes a handle 4, a catheter 6 connected to the handle 4, and a stapler head 8 connected to both the handle 4 and the catheter 6. The surgical stapling tool 2 may be configured differently, if desired. The handle 4 and the stapler head 8 are both fixed to the catheter 6. Alternately, the handle 4 and/or the stapler head 8 may be detachable from the catheter 6 to allow for interchangeability of these components. At least part of the handle 4 and/or the stapler head 8 may be constructed from materials that can be sterilized, such as by an autoclave, and reused. The handle 4 may assume any appropriate configuration; the shape and configuration of the handle 4 described herein is exemplary and not limiting. The handle 4 may include a trigger 10 that provides for actuation of the surgical stapling tool 2 based solely on a single input from the user to that trigger 10, as described in greater detail below. Alternately, one or more other or additional inputs may be utilized to actuate the surgical stapling tool 2. For example, actuation of the surgical stapling tool 2 may be based on an input to one or more buttons in addition to the trigger 10.

Figure 2:
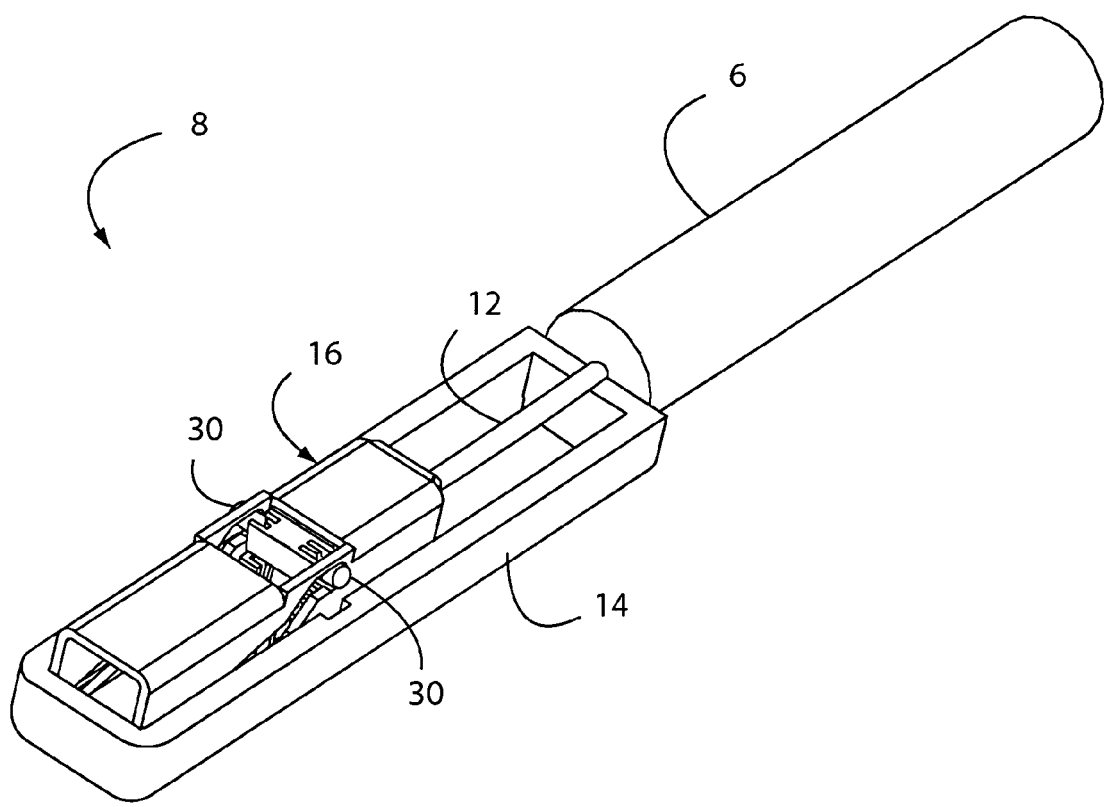
FIG. 2 is a perspective cutaway view of the stapler head of FIG. 1.

The catheter 6 is a standard catheter such as used in coronary or peripheral vascular procedures. As such, the catheter 6 is stiff enough to push the stapler head 8 to the desired position in the vasculature through an opening in the femoral artery or other arty, and flexible enough to move through the vasculature without damaging the tissue thereof. The catheter 6 is non-rigid. The catheter 6 is a tubular structure having one or more lumens therethrough. Alternately, the catheter 6 may be configured in any other suitable manner. Referring also to FIG. 2, one or more force transmission members 12 extend through at least one lumen of the catheter 6. Advantageously, a single force transmission member 12 is utilized. Where multiple force transmission member 12 are utilized, each force transmission member 12 may extend through a separate lumen of the catheter 6, or multiple force transmission members 12 may extend through one lumen of the catheter 6. At least one force transmission member 12 may be a cable 12, such as a braided stainless steel wire cable. The catheter 6 may be configured to accommodate a standard guidewire that may be used to guide the catheter 6 and stapler head 8 to a treatment site. As one example, the catheter 6 may include a lumen therein that is configured to receive and travel along the guidewire. As another example, a tube or tubes may be attached to the outer surface of the catheter 6, where such a tube or tubes receive the guidewire.

Referring also to FIG. 2, the stapler head 8 may be attached to the distal end of the catheter 6. The stapler head 8 may be attached to the stapler head 8 in any suitable manner. Alternately, the stapler head 8 may be attached to the catheter 6 at a location other than the distal end of the catheter 6. The stapler head 8 includes a housing 14. A portion of the housing 14 is cut away to better illustrate the interior of the stapler head 8. The housing 14 may have any suitable shape. As one example, the housing 14 is shaped as the shell of a substantially rectangular solid, with smoothed or curved vertices to protect tissue. At least one force transmission member 12 may extend out of the distal end of the catheter 6 into the interior of the housing 14.

Figure 3:
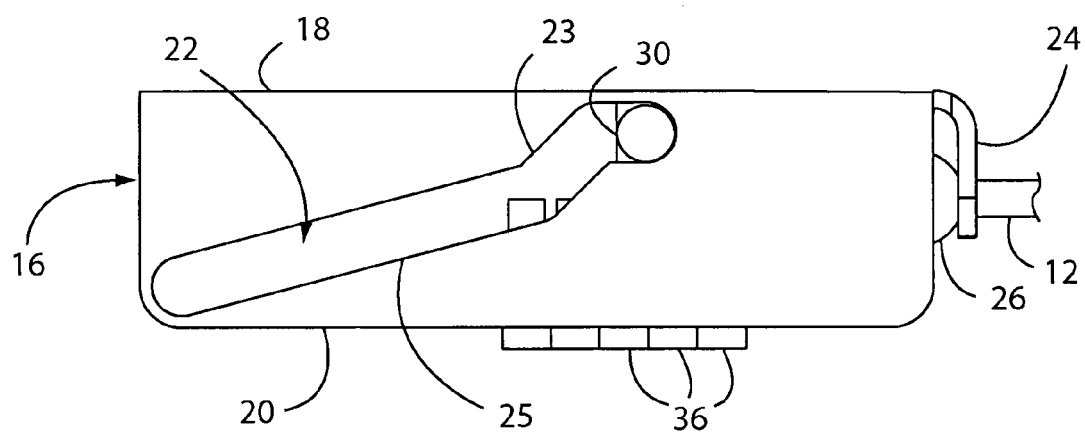
FIG. 3 is a side view of a slider of the stapler head in a first position.

Referring also to FIG. 3, a slider 16 is movable within the housing 14, and may be connected to at least one force transmission member 12. The slider 16 may be substantially U-shaped as viewed longitudinally, with an upper surface 18 and two walls 20 extending downward from the upper surface 18, one from either edge of the upper surface 18. The terms "upper," "lower," "downward," "upward," "vertical," "horizontal" and the like are used for convenience only, in reference to the position of various components in the Figures. The use of these terms does not limit the orientation of the stapler head 8 in use. Alternately, the slider 16 may be shaped differently. At least one wall 20 of the slider 16 includes at least one slot 22 defined therein. A proximal wall 24 may extend downward from the upper surface 18 at or near the proximal end of the slider 16. The proximal wall 24 may be connected to at least one force transmission member 12 in any suitable manner. As one example, the force transmission member 12 may be a cable 12 that extends through an opening (not shown) in the proximal wall 24 and is crimped to the proximal wall 24. As another example, an end of the cable 12 is connected to an termination element 26. The termination element 26 is wider than the opening in the proximal wall 24 through which the cable 12 extends. Thus, the termination element 26 prevents the cable 12 from slipping out of the opening in the proximal wall 24. As another example, the end of the cable 23 may be knotted, forming a knot having a diameter larger than that of the opening in the proximal wall 24. As another example, the cable 12 is connected to the proximal wall by welding or by adhesive. The cable 12 is routed into the stapler head 8 in such a way that tension exerted on the cable 12 causes the slider 16 to move proximally. Alternately, at least one force transmission member 12 is connected to a different location on the slider 16, directly or indirectly.

Figure 4:
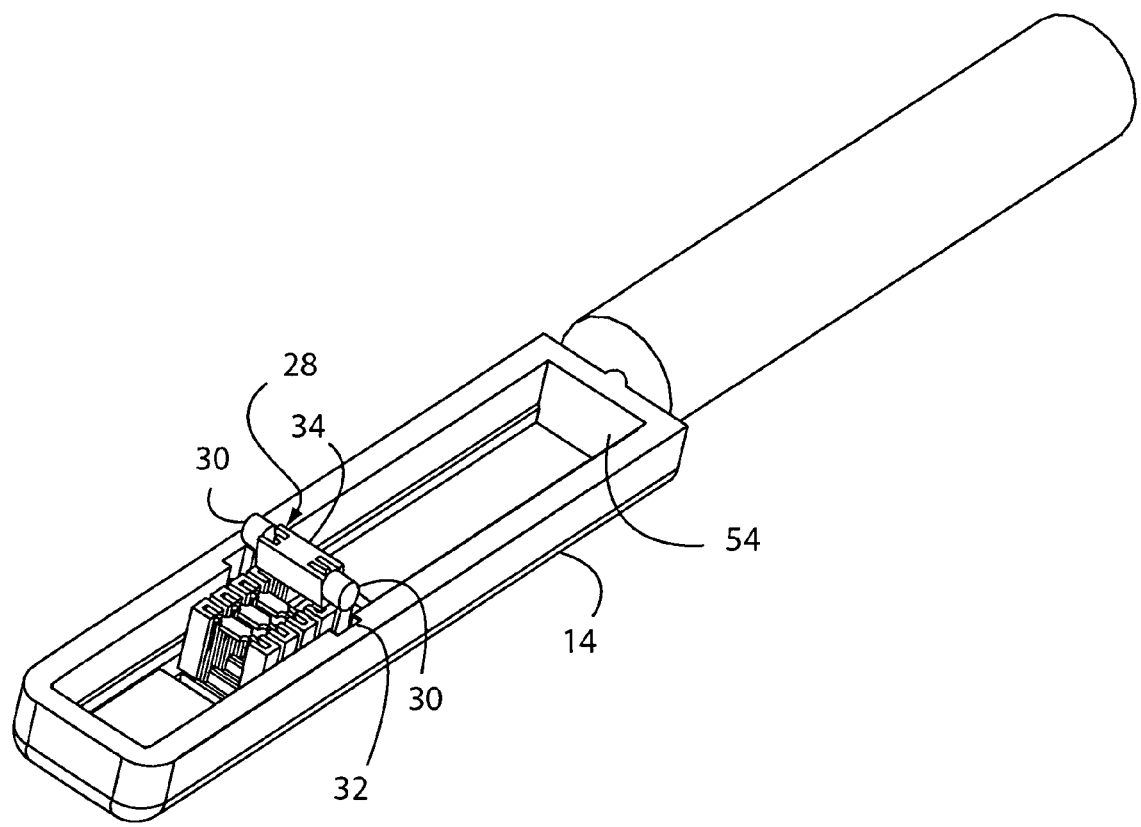
FIG. 4 is a perspective cutaway view of the stapler head of FIG. 1, with the slider omitted for clarity.

Referring also to FIG. 4, a driver 28 is movable within the housing 14. The driver 28 includes at least one post 30 extending laterally from a central body 34. Each post may be substantially cylindrical, or may be shaped differently. At least one groove 32 is defined in the inner surface of the housing 14, oriented substantially in the vertical direction. Each groove 32 is sized and shaped to receive a corresponding post 30 of the driver 28. Advantageously, posts 30 extend laterally from the driver 28 in both directions, and each is received in the corresponding groove 32 in the housing. The groove 32 constrains motion of the corresponding post 30 along the direction of the groove 32. Thus, the use of two substantially vertical grooves 32 with a driver 28 having two lateral posts 30 extending therefrom constrains the motion of the driver 28, allowing the driver 28 to move up and down along the grooves 32 but substantially restricting the motion of the driver 28 in the longitudinal or lateral directions. That is, the driver 28 is constrained to move substantially perpendicular to the longitudinal axis of the stapler head 8. Alternately, the grooves 32 are oriented differently, and thereby constrain the motion of the driver 28 differently.

Figure 9:
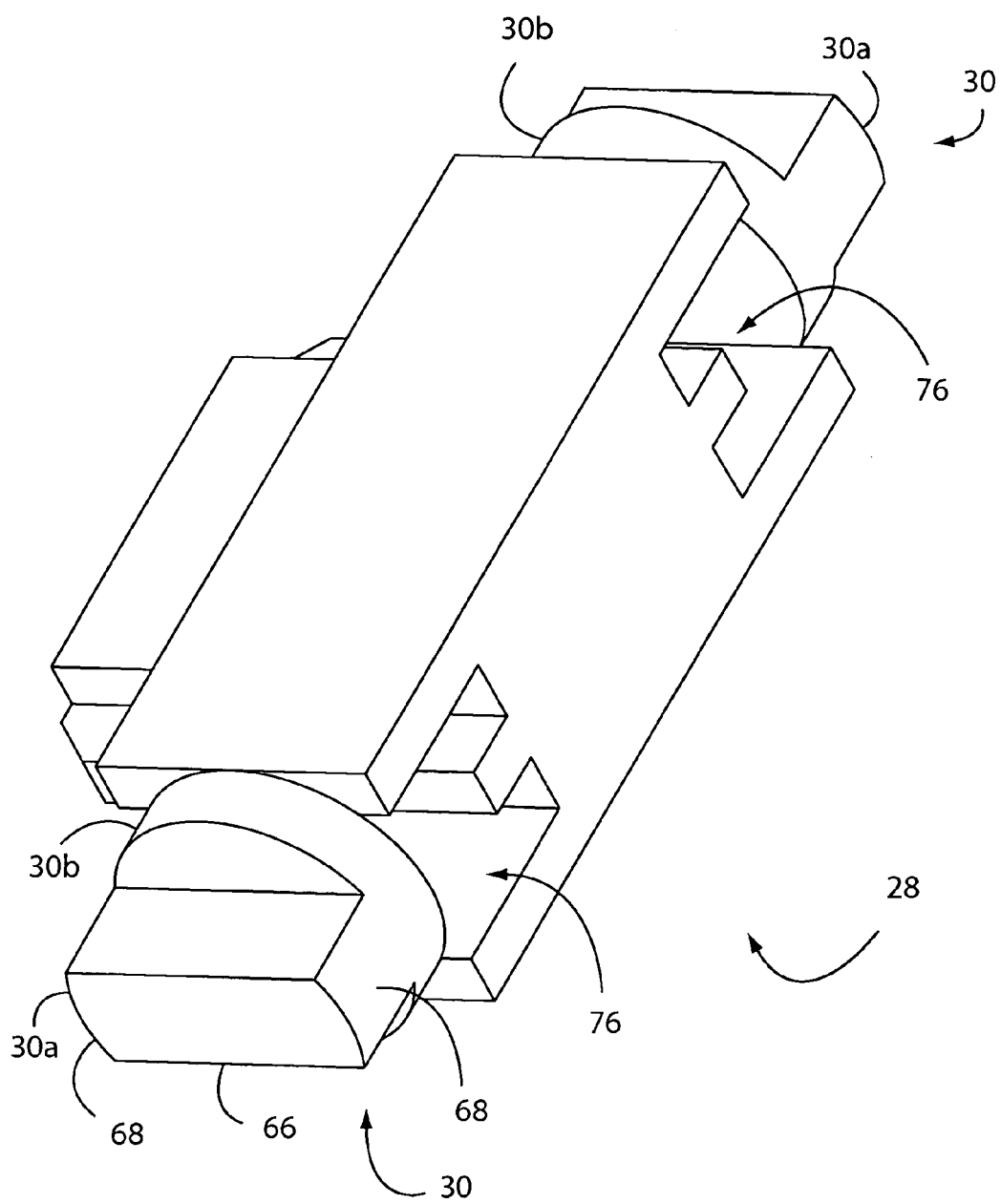
FIG. 9 is a perspective view of an embodiment of a driver that may be used within an exemplary stapler head.

Optionally, referring also to FIG. 9, at least one post 30 includes a dog 30a extending from a base 30b. The base 30b may be substantially cylindrical, or may be shaped in any other suitable manner. Each base 30b is sized to engage a corresponding slot 22 defined in the slider 16, and advantageously does not engage the corresponding groove 32 in the housing 14. The dog 30a extending from the base 30a is in turn shaped and sized to engage the corresponding groove 32 in the housing 14. As one example, the dog 30a may have two substantially flat opposed first sides 66, separated by two curved second sides 68 that may smoothly extend from the base 30b.

Figure 10:
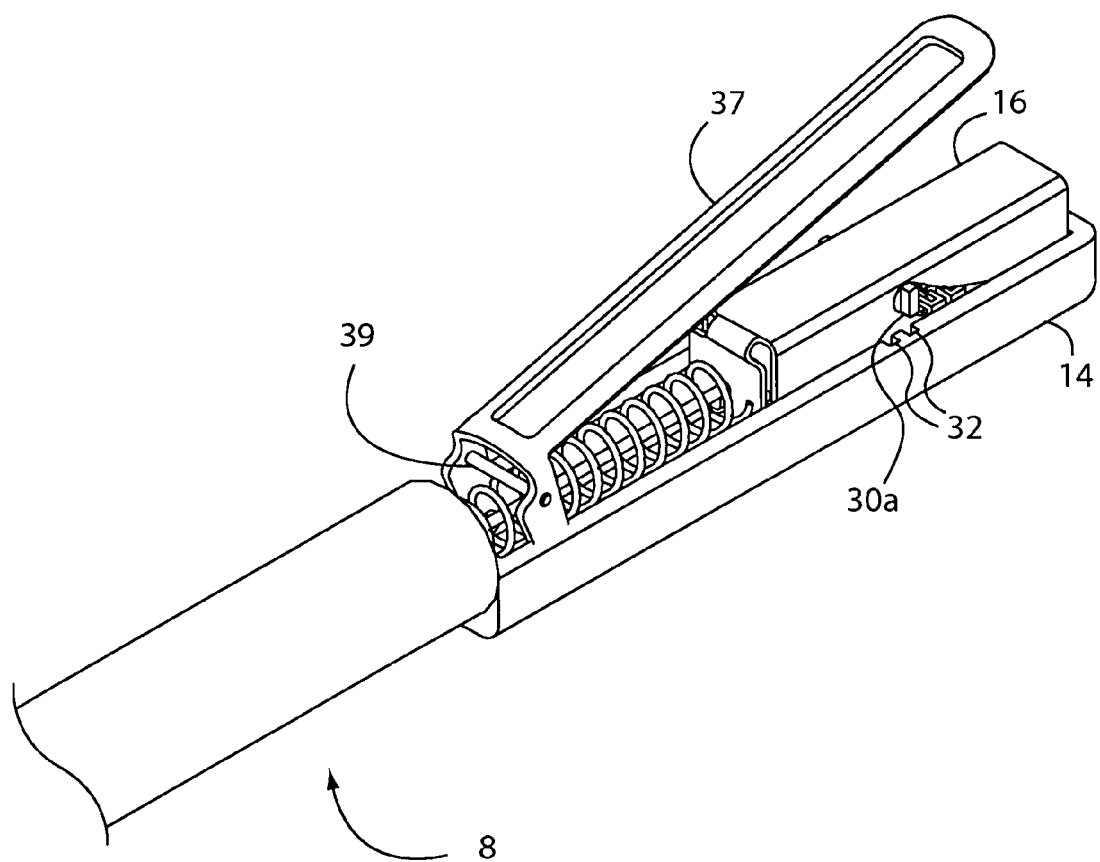
FIG. 10 is a partial cutaway perspective view of an exemplary stapler head.
Figure 11:
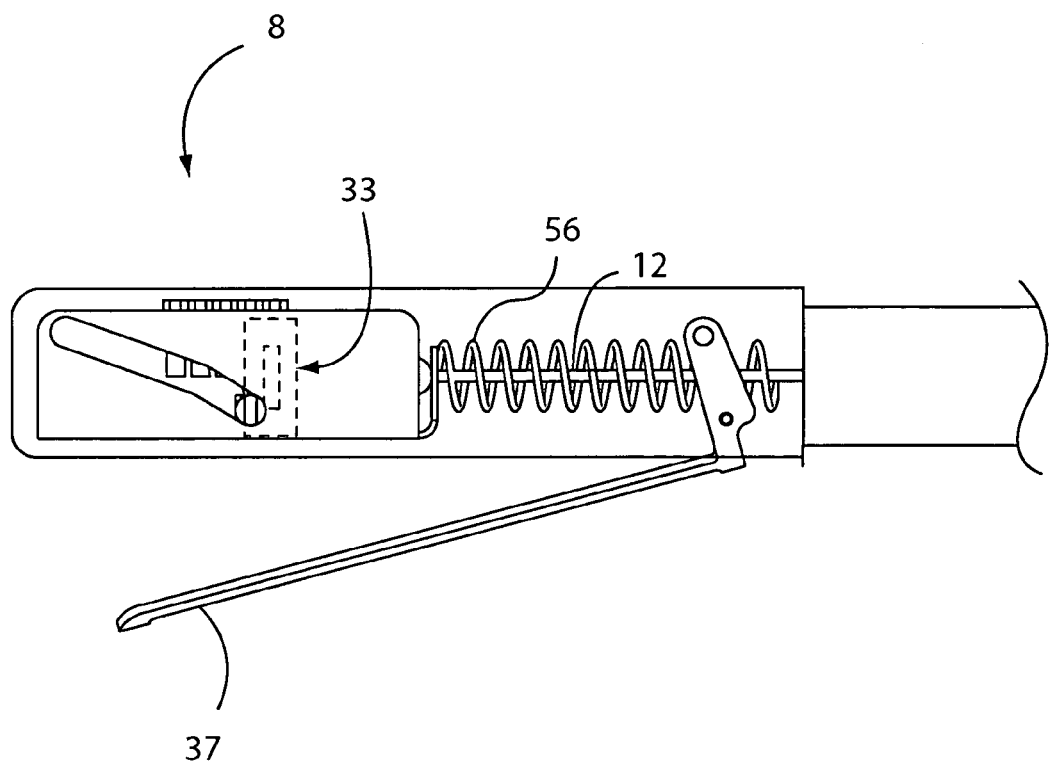
FIG. 11 is a side cutaway view of the stapler head of FIG. 10.

Referring also to FIGS. 10-11, each groove 32 in the housing 14 may define a closed polygonal or curved shape, which may be referred to as a race 33. Advantageously, one race 33 is defined in each side of the housing 14, and each race 33 is shaped substantially the same. Each race 33 may be shaped in any suitable manner. As one example, each race 33 is rectangular, having a length dimension measured along the longitudinal axis of the stapler head 8 that is less than the height dimension of the race 33. However, other shapes or configurations may be utilized. Where the race 33 is substantially rectangular, the sides of the race 33 extending substantially vertically may have a width that is slightly greater than the distance between the two substantially flat opposed first sides 66 of the dog 30a, and the sides of the race 33 extending substantially horizontally may have a width that is slightly greater than the distance between the two curved second sides 68 of the dog 30a. In this way, motion and orientation of the dog 30a relative to the race 33 can be controlled, as described in greater detail below.

Referring also to FIG. 3, at least part of the driver 28 may be positioned within the slider 16. That is, the driver 28 may be positioned below the upper surface 18 of the slider 16, and between the walls 20 of the slider 16. Each post 30 of the driver 28 extends through a corresponding slot 22 in the wall 20 of the slider 16, then into the corresponding groove 32 in the housing 14. In this way, at least one wall 20 is positioned between the central body 34 of the driver 26 and a groove 32 in the inner surface of the housing 14.

Figure 5:
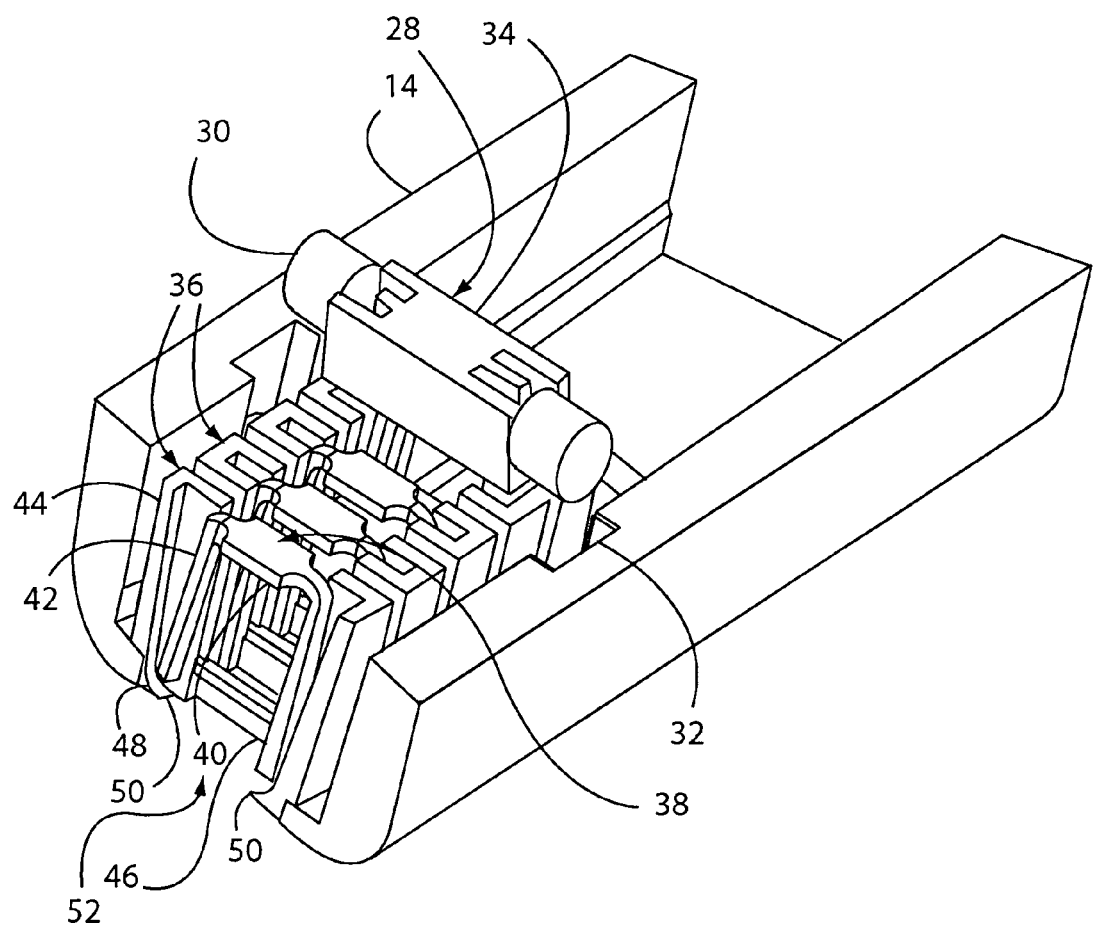
FIG. 5 is a detail perspective cutaway view of the stapler head of FIG. 1, with the slider and the distal end of the stapler head omitted for clarity.

Referring to FIGS. 4-5, at least one holder 36 is positioned within the housing 14. Each holder 36 holds a staple 38. The staples 38 may be shaped in any suitable manner, and at least one staple 38 may be shaped differently than one or more other staples 38. As one example, at least one staple 38 has a substantially planar base 40, with a tine 42 extending laterally from each side of the base 40. Each tine 40 is narrower than the width of the base 40, as measured in the longitudinal direction. Alternately, at least one staple 38 is configured differently.

Each holder 36 may be shaped in any manner that allows it to hold a staple 38, and at least one holder 36 may be shaped differently than one or more other holders 36. As one example, a holder 36 may include two substantially upwardly-extending columns 44 connected to a substantially laterally-extending base 46. The columns 44 may have a generally U-shaped profile looking downward into them, where a tine 42 of the staple 38 is held by a column 44 between the arms of the U. The open sides of the U-shaped columns 44 face each other, such that each column 44 of a holder 36 holds a tine 42 of the corresponding staple 38. Alternately, the columns 44 are configured differently to hold the corresponding staple 38. The inner surface of each column 44 facing the longitudinal centerline of the housing 14 may be a ramp element 48. The ramp element 48 is smoothly curved inward, moving downward along the column 44. That is, the distance between two opposed ramp elements 48 in a holder 36 is less at the bottom of the holder 36 than at the top of the holder 36. This curvature assists in deployment of the staple 38. At the bottom of the holder 36, each ramp element 48 terminates in a foot 50. Taken together, the feet 50 of each holder 36, in conjunction with a portion of each ramp element 48 in proximity to each foot 50, may be characterized as an internal anvil. Thus, at least one holder 36 includes an internal anvil for forming the staple 38 deployed therefrom.

The base 46 of at least one holder 36 may be two substantially laterally-extending bars on opposite sides of two laterally-spaced columns 44. Advantageously, the holder 36 is fabricated from a single piece of material, but the columns 44 and base 46 initially may be separate pieces that are connected in any suitable manner. The base 46 of each holder 36 contacts the base 46 of at least one adjacent holder 36. In this manner, force between adjacent holders 36 is transmitted between the bases 46 of those holders 36. Alternately, adjacent holders 36 contact one another in one or more different or additional locations. The holders 36 separate adjacent staples 38 from one another such that force is transmitted between holders 36, not between staples 38. That is, where a longitudinal force is applied to one holder 36, that force is transmitted to the adjacent holder 36 without exerting any force on the staple 38 within each holder 36. In this way, the design and fabrication of the staples 38 may be simplified, as the staples 38 do not transmit forces among one another. That is, each holder 36 substantially isolates the staple 38 that it holds from force transmitted from any adjacent holder 36. The staples 38 may be spaced apart from one another without touching, as a result of their being held within the holders 36. Alternately, at least one staple 38 may contact one or more adjacent staples 38.

Where more than one holder 36 is utilized, they are arranged longitudinally, such that one holder 36 is the most proximal holder 36, and that one holder 36 is the most distal holder 36. Alternately, at least one of the holders 36 may be positioned differently relative to at least one of the other holders 36. The holder or holders 36 are positioned within the housing 14 such that the upper boundary of each holder 36 is at a lower height than the lower boundary of the driver 28, when the driver 28 is in a ready position. In the ready position, the driver 28 is above the staple 38, but is not applying a deployment force to the staple 38. Alternately, the holder or holders 36 may be positioned differently within the housing 14. An ejection aperture 52 is defined through the bottom surface of the housing 14. The ejection aperture 52 is directly underneath the driver 28, such as where the groove or grooves 32 are substantially vertical. Alternately, the longitudinal position of the ejection aperture 52 may be offset from the longitudinal position of the driver 28. Because the driver 28 is constrained to move along the groove or grooves 32, the ejection point of each staple 38 from the corresponding holder 36 is always known, and that ejection point is the ejection aperture 52.

Figure 12:
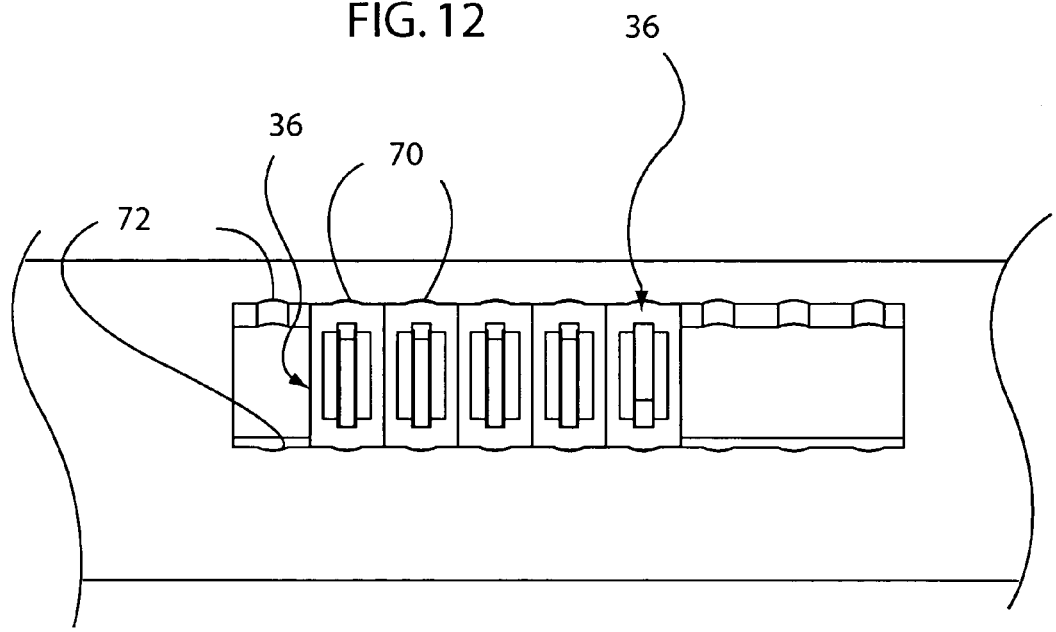
FIG. 12 is a perspective view of a portion of the bottom of the stapler head of FIG. 10.
Figure 13:
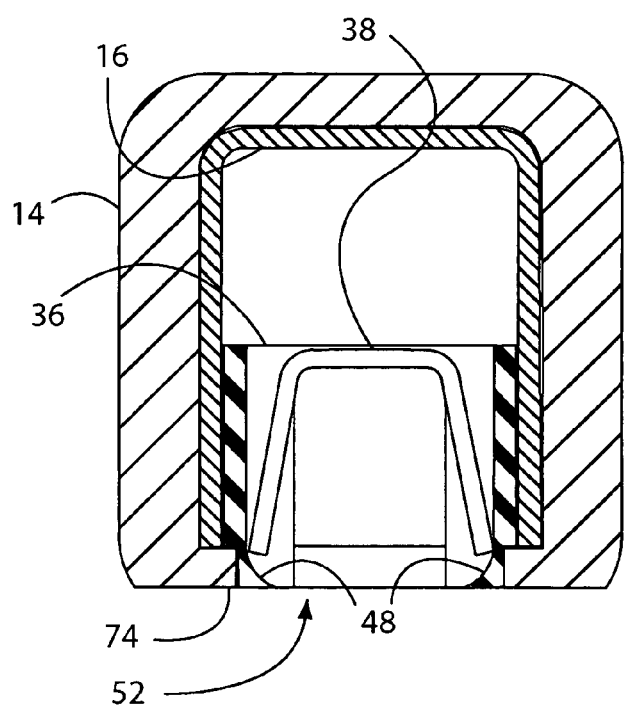
FIG. 13 is a cross-section view of the stapler head of FIG. 12.

As another example, the holders 36 may be connected together or fabricated as a single unit or cartridge. Where the holders 36 together form a cartridge, that cartridge may be replaceable, such that the surgical stapling tool 2 may be sterilized, loaded with a new cartridge of holders 36 carrying staples 38, and reused. As another example, the cartridge is not replaceable, and the surgical stapling tool 2 is a single-use tool that is used once and discarded. Referring also to FIGS. 12-13, at least one holder 36 may include at least one detent 70 extending therefrom. Advantageously, each holder 36 may includes one detent 70 extending from each side thereof. Each detent 70 is configured to engage a corresponding receiver 72 defined in the slider 16. The detents 70 on each side of the set of holders 36 are spaced apart from one another a distance substantially equal to the distance that the receivers 72 are spaced apart on the slider 16. Alternately, the detents 70 are provided on the slider 16, and the corresponding receivers 72 are provided on the holders 36. A ledge 74 on at least one side of the slider 16 extends inward underneath the holders 36, and thereby may assist in retaining the holders 36 within the slider 16. Advantageously, both sides of the slider 16 includes a ledge 74 extending therefrom.

Figure 6:
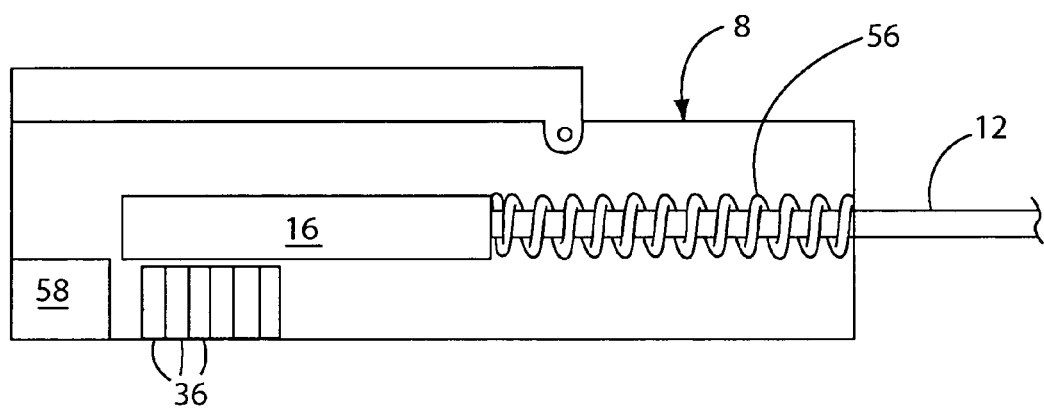
FIG. 6 is a schematic view of an exemplary stapler head.

Referring to FIG. 6, the slider 16 may be biased distally by a biasing element 56. As one example, the biasing element 56 may be a compression spring positioned between the proximal wall 24 of the slider 16 and the rear wall 54 of the inner surface of the housing 14. The compression spring may be substantially concentric with the force transmission member 12, or may be offset from the force transmission member 12. Alternately, the biasing element 56 may be any other structure, mechanism or combination thereof that biases the slider 16 distally. Alternately, the biasing element 56 may be omitted, such that the slider 16 is not biased distally.

The holders 36 may be indexed in the proximal direction. That is, an indexing mechanism 58 may be configured to move the holders 36 collectively in the proximal direction, one holder 36 at a time. This discrete motion of the holders 36 may be referred to as indexing. The indexing mechanism 58 moves the holders 36 sequentially into position over the ejection aperture 52, or facilitates this motion. The indexing mechanism 58 may be any mechanism capable of doing so. As one example, the indexing mechanism 58 may include a ratchet mechanism. A second force transmission member may be connected to the indexing mechanism 58, and may move proximally a distance substantially equal to the width of one holder 36 in order to index the holders 36. The second force transmission member may be controlled by a piston, spring, stepper motor or other suitable mechanism in the handle 4 or elsewhere.

The stapler head 8 may include a stabilizer 37. The stabilizer 37 is movable from a first position to a second position in order to stabilize the stapler head 8 in use, as described in greater detail below. The stabilizer 37 may be any mechanism that is configured to stabilizer the stapler head 8. As one example, the stabilizer 37 is a paddle or similar device movable relative to the stapler head 8. Referring also to FIG. 10, the stabilizer 37 may be substantially U-shaped, with the open end of the U-shape connected to the remainder of the stapler head 8. The stabilizer 37 may be hinged or otherwise connected to the remainder of the stapler head 8, and may rotate about any axis or axes, or move in any suitable direction, between the first position and the second position. Optionally, a biasing element such as a spring may bias the stabilizer 37 to the first, stowed position. A cable or other force transmission member 12 may connect the stabilizer 37 to the handle 4 directly or indirectly, such that the force transmission member 12 controls the position of the stabilizer 37. As one example, the cable or force transmission member 12 may be connected to a crossbar 39 of the stabilizer 37 that is offset from the axis of rotation of the stabilizer 37 about a remainder of the stapler head 8. In order to deploy the stabilizer 37, the cable 12 simply may be moved proximally, exerting a force on the crossbar 39 that generates a moment that causes the stabilizer 37 to rotate about its hinged connection to the remainder of the stapler head 8, or otherwise move relative to the remainder of the stapler head 8. Alternately, where a rigid force transmission member 12 is connected to the stabilizer 37, the force transmission member 12 may be moved distally to move the stabilizer 37 to the second position. Alternately, the stabilizer 37 may be a balloon or other inflatable structure that is connected to the stapler head 8, such as to the upper surface of the stapler head 8. The balloon 37 may be inflatable to stabilize the stapler head 8 in a desired location, and deflatable to allow movement of the stapler head 8 to a treatment site. The balloon 37 may be inflated by a fluid source in the handle 4, particularly where the handle 4 includes a fluid-driven actuator for actuating the stapler head 8; fluid such as pressurized gas may be transmitted to and from the balloon 37 via a lumen of the catheter 6. Alternately, the pressurized gas source or other fluid source may be located substantially within the stapler head 8. Alternately, the stabilizer 37 is not used. Alternately, the surgical stapling tool 2 includes two opposed stapler heads 8 facing in substantially opposite directions, where neither stapler head 8 includes a stabilizer 37 The stapler heads 8 may be movable apart from and/or biased apart from one another, such that when both stapler heads 8 are in contact with tissue, each stapler head 8 stabilizes the other.

Operation

Figure 8:
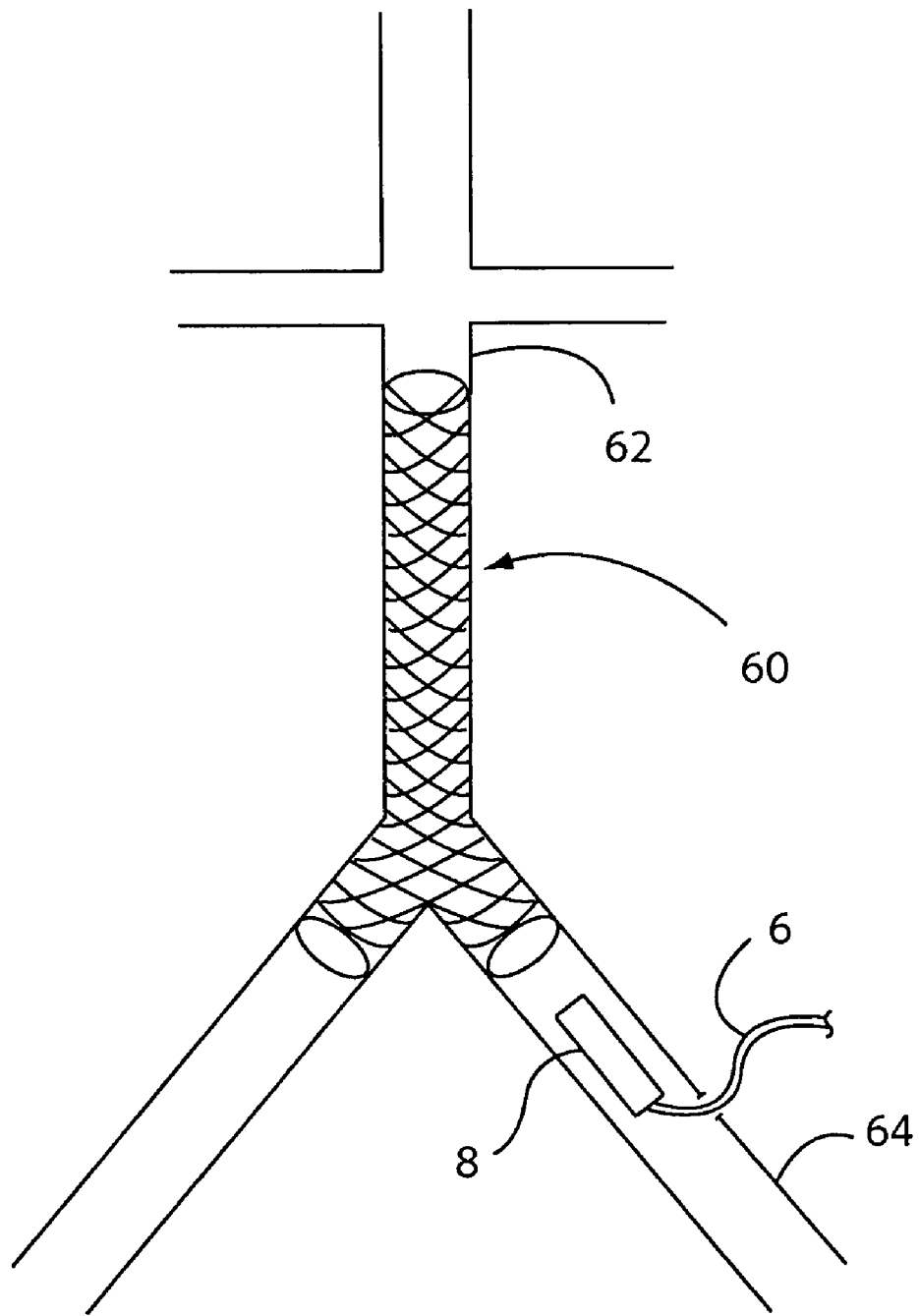
FIG. 8 is a schematic view of the placement of an AAA graft in the abdominal aorta utilizing the surgical stapling tool.

Referring also to FIG. 8, to introduce the stapler head 8 into the vasculature of a patient, an incision 65 is made in the patient's femoral artery 64 in a standard manner. For the purpose of describing the operation of the surgical stapling tool 2, the placement of a AAA graft 60 will be described. However, the surgical stapling tool 2 may be utilized at a different location in the patient's vasculature. Further, the surgical stapling tool 2 may be introduced into the vasculature via the radial artery or other blood vessel. Before inserting the stapler head 8 into the femoral artery 64, a AAA graft 60 may be advanced through the opening in the femoral artery into the abdominal aorta 62 and placed in its desired location. Alternately, the AAA graft 60 may be moved into its desired position in the aorta 62 along with the stapler head 8. Alternately, the AAA graft 60 may be moved into its desired position in the aorta 62 after the stapler head 8 has been moved into position.

The stapler head 8 is inserted through the opening in the femoral artery and advanced upward by pushing on the catheter 6. The catheter 6 may be configured to follow a guidewire that has been previously placed in the patient according to standard interventional cardiology practice, or may be configured to be advanced regardless of the presence of a guidewire. The stapler head 8 is thus advanced through the femoral artery into the abdominal aorta. Any suitable technique may be utilized to place the stapler head 8 in the desired position in the abdominal aorta. For example, at least part of the stapler head 8 may be radiopaque, such that an x-ray machine or the like in the operating room may be used to determine when the stapler head 8 has reached its final position.

When the stapler head 8 reaches its desired position, the stabilizer 37 is deployed, moving from a first (stowed) position to a second (stabilizing) position. Such deployment may be performed in any suitable manner. As one example, where the stabilizer 37 is a paddle or similar device movable relative to the stapler head 8, a cable or force transmission member that connects the stabilizer 37 to the handle 4 directly or indirectly may be moved. As a result of motion of that cable or force transmission member, the stabilizer 37 may rotate, expand or otherwise move into contact with an inner surface of the wall of the aorta 62, thus moving from the first position to the second position. For example, referring also to FIG. 10, motion of a cable or other force transmission member 12 simply pulls the stabilizer 37 about a hinge or other member to the second position. This contact between the stabilizer 37 and the wall of the aorta 62 pushes the stapler head 8 into contact with a different part of the wall of the aorta 62 and/or with the AAA graft 60, such that the ejection aperture 52 is substantially adjacent to the wall of the aorta and/or the AAA graft 60. Alternately, where the stabilizer 37 is a balloon, the stabilizer is inflated from the first position to the second position. Alternately, where the stabilizer 37 is a different mechanism, the stabilizer 37 is actuated in any suitable manner. Alternately, where the stabilizer 37 is omitted, and two opposed stapler heads 8 are provided, the stapler heads 8 are moved apart from one another, such that each stapler head 8 contacts the wall of the aorta 62 and stabilizes the other. Optionally, the stapler head 8 and/or the handle 4 may include a safety mechanism that prevents deployment of a staple 38 until the stabilizer 37 is deployed. The use of a substantially U-shaped stabilizer 37 or stabilizer 37 having an open area may facilitate the flow of blood or other fluid through part of the stabilizer 37, thereby reducing or minimizing drag resulting from contact between flowing bodily fluid and the stabilizer 37. Alternately, the stabilizer 37 may not include an open area, but may be sized and/or shaped to reduce or minimize drag resulting from contact between flowing bodily fluid and the stabilizer 37. In this way, minimally invasive intravascular surgery such as within the aorta may be facilitated, as the stapler head 8 may be placed in a suitable position within the aorta without the need to stop blood flow therein.

Initially, the slider 16 is in an initial position, as shown in FIGS. 2-3. In the initial position of the slider 16, each post 30 of the driver 28 is positioned at the proximal end of the corresponding slot 22 in the wall 20 of the slider 16. The slot 22 is shaped to facilitate deployment of staples 38, as described in greater detail below. When the slider 16 is in the initial position, a holder 36 is positioned directly below the driver 28, and may be said to be in firing position. When the holder 36 is in firing position, it is above the ejection aperture 52 in the lower surface of the housing 14. Further, the driver 28 is initially in a ready position above the holder 36. The ready position may be the uppermost position that the driver 28 can occupy, or may be a different vertical position relative to the housing 14.

The user depresses the trigger 10, manipulates a different control, or otherwise actuates the surgical stapling tool 2 after the stapler head 8 has reached the desired position. In this way, the surgical stapling tool 2 may be actuated with a single input from a user. In response, the handle 4 moves the force transmission member 12 proximally. For example, where the force transmission member 12 is a cable, the handle 4 applies tension to that cable, moving it proximally. This proximal motion of the force transmission member 12 moves the slider 16 proximally. Each post 30 of the driver 28 is constrained against horizontal motion and restricted to vertical motion by the corresponding groove 32. Thus, as the slider 16 moves proximally, each slot 22 in the wall 20 of the slider 16 acts to move the corresponding post 30 vertically. That is, the shape of the slot 22 controls the vertical motion of the corresponding post 30, and thus the vertical motion of the driver 28.

The exemplary slot 22 may be substantially horizontal for a short distance extending distally from its proximal end, such that proximal motion of the slider 16 initially does not move the corresponding post 30 and thus the driver 28 vertically. This horizontal portion of the slot 22 provides extra safety, such that negligible motion of the force transmission member 20 does not cause vertical motion of the driver 28.

Looking distally along the slider 16, a first portion 23 of the slot 22 extends downward at a first angle from horizontal. As the first portion 23 of the slot 22 is pulled proximally, the first portion 23 urges the corresponding post 30 downward in the corresponding groove 32, thus urging the driver 28 downward. The driver 28 contacts the base 40 of the staple 38 that is located in the holder 36 in firing position. Advantageously, the shape of the driver 28 and the shape of the base 40 facilitate contact and force transmission therebetween. For example, where the base 40 of the staple is substantially rectangular, the driver 28 may include a substantially rectangular surface that is similar in size to the base 40 of the staple 40 to spread the contact force therebetween over a larger area.

As the driver 28 continues to move downward, it pushes the staple 38 within the holder 36 toward the ejection aperture 52. The end of each tine 42 of the staple 38 contacts the corresponding ramp element 48 of the holder 36. This contact causes each tine 42 to begin to bend as the staple 38 moves toward the ejection aperture 52. Referring also to FIG. 8, as the tines 42 move out of the ejection aperture 52, they penetrate the AAA graft 60, and then the tissue of the aorta 62. The angle of each slot 22 immediately distal to the horizontal portion of the slot 22 assists in the penetration of the AAA graft 60 and the tissue of the aorta 62 by causing substantial vertical motion in a short period of time. That is, because the slider 16 may be moved horizontally by the force transmission member 12 at substantially a constant rate, the angle of the slot 22 relative to the horizontal at any given point controls the rate of vertical motion of the driver 28. The greater the angle from horizontal, the more rapid the vertical motion.

Moving further distally along the slider 16, a second portion 25 of the slot 22 extends downward at a second angle from horizontal. As the second portion 25 of the slot 22 is pulled proximally, the second portion 25 urges the corresponding post 30 downward in the corresponding groove 32, thus continuing to urge the driver 28 downward. The second angle is less than the first angle, relative to the horizontal. The second portion of each slot 22 immediately distal to the first portion of that slot 22 spreads vertical motion of the driver 28 over a longer time than the first portion of that slot 22, because the force required for forming the staple 38 is less than the potential force required to urge the tines 42 of the staple 38 through the AAA graft and the tissue of the aorta. Alternately, the second angle is the same as the first angle, or is greater than the first angle. As the driver 28 continues to move downward, it continues to push toward the ejection aperture 52 the staple 38 that is within the holder 36 underneath the driver 28. The end of each tine 42 of the staple 38 continues to contact the corresponding ramp element 48 of the holder 36 as the driver 28 continues to move downward. This contact causes each tine 42 to continue to bend as the staple 38 moves toward the ejection aperture 52. The curvature of each ramp element 48 in proximity to the corresponding foot 50 determines the path along which each tine 42 travels as it moves through the AAA graft and the tissue of the aorta. Advantageously, the curvature of each ramp element 48 in proximity to the corresponding foot 50 directs the corresponding tine 42 along a path that does not snag tissue outside of the aorta.

Each foot 50 controls the entry point of the corresponding tine 42 into tissue, and controls the path of each tine 42 into tissue during staple forming. In this way, the feet 50 prevent bunching of the tissue as the staple 38 is formed. Bunching refers to the undesirable effect on tissue of the tines of a traditional surgical staple when the staple is closed and the tines are brought closer together. With a traditional staple and stapler, this motion pushes tissue between the tines together, thereby bunching the tissue, and also may create holes in tissue as the tines stretch tissue that is not trapped between the tines. Each foot 50 provides a known location at which the tine 42 is controlled to exit the corresponding holder 36. That is, each foot 50 guides the corresponding tine 42 through tissue substantially along a path determined by that foot 50. As a result, during staple forming, the location of each tine 42 relative to its penetration of tissue is substantially constant. That is, the location on the tissue that is penetrated by the tine 42 of a staple 38, which may be referred to as the tine entry point, is substantially constant throughout the process of deploying the staple 38. The tine entry point is not substantially enlarged or moved during deployment. Because the location at which each tine 42 penetrates the tissue of the aorta 62 is substantially the same throughout the staple forming process, bunching is substantially prevented.

Figure 7:
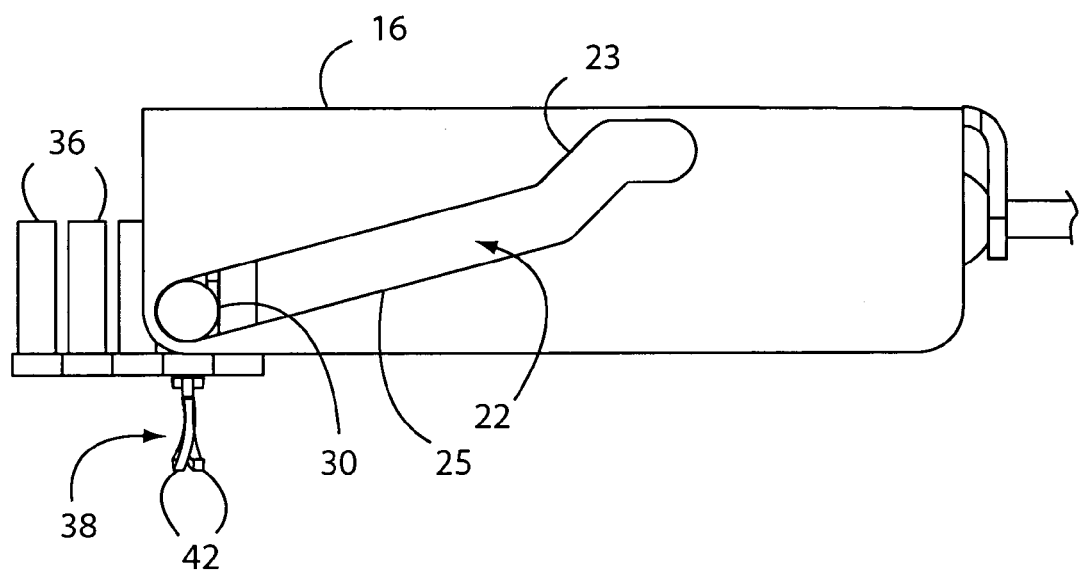
FIG. 7 is a side view of a slider of the stapler head in a second position.

Referring also to FIG. 7, as the staple 38 is formed, the tines 42 swipe past each other. In this way, the tines 42 do not substantially interfere with one another, substantially preventing uncontrolled deflections that may result from such interference. The tines 42 may be configured to swipe past one another in any suitable manner. As one example, the ramp elements 48 are angled differently from one another and/or the feet 50 are slightly offset from one another, such that the tines 42 are controlled to swipe past one another. As another example, the staple 38 is fabricated to result in the tines 42 swiping past one another. The staple 38 may be fabricated such that the tines 42 are offset from one another before deployment; cutouts or weakened areas in one or both tines 42 of the staple 38 may provide for preferential bending of the tines 42 in directions that result in the tines 42 swiping past each other, or the staple 38 may have other properties that result in its tines 42 swiping past each other.

Referring also to FIG. 7, the slider 16 has reached the end of its travel, with at least one post 30 of the driver 28 contacting the distal end of the corresponding slot 22. At this point, the staple 38 is fully formed. The process of urging the tines of the staple 38 into tissue and forming the staple 38 may be referred to as deployment. The feet 50 and ramp elements 48 may control the tines 42 such that their ends are substantially tangent to the outer surface of the wall of the aorta and such that the tines 42 lie against or close to the outer surface of the wall of the aorta. Thus, after the staple 38 has been fully formed, it secures the AAA graft to the wall of the aorta, and is itself secured to tissue. Nothing remains to hold the staple 38 within the holder 36, and the base 40 of the staple 38 moves out of the bottom of the holder 36 and through the ejection aperture 52. The staple 38 is thus released from the stapler head 8.

Next, tension on the force transmission member 12 is released. As a result, the force transmission member 12 exerts no force or a reduced force in the proximal direction on the slider 16. The biasing element 56 exerts a distal force on the slider 16, moving it back toward its initial position. Alternately, the force transmission member 12 is substantially rigid and is moved distally, and the biasing element 56 is omitted. As the slider 16 moves distally, each post 30 of the driver 28 moves along the corresponding slot 22 in a manner opposite to its motion during deployment of the staple 38, such that the driver 28 moves upward to its initial position as a result. Next, the indexing mechanism 58 moves the holders 36 collectively in the proximal direction, by a distance substantially equal to the width of one holder 36. In this way, another holder 36 containing a staple 38 may be moved into the firing position between the driver 28 and the ejection aperture 52. As one example of operation, a second force transmission member is connected to the indexing mechanism, and moves proximally a distance substantially equal to the width of one holder 36 in order to index the holders 36. The second force transmission member may be controlled by a piston, spring, stepper motor or other suitable mechanism in the handle 4 or elsewhere. As another example, a biasing element acts in concert with a ratchet mechanism in the stapler head 8 to index the holders 36. The holders 36 may be indexed in any suitable manner. The stapler head 8 is thus ready to fire again, utilizing the process described above.

Alternately, the driver 28 is configured such that at least one post 30 includes a dog 30a connected to a base 30b, where the dog 30a is movable along a race 33, as described above. If so, operation of the stapler head 8 proceeds substantially as described above. Initially, the slider 16 is in an initial position, as shown in FIG. 11. When the slider 16 is in the initial position, each base 30b of the driver 28 is positioned at the proximal end of the corresponding slot 22 in the wall 20 of the slider 16. Further, when the slider 16 is in the initial position, a holder 36 is in firing position above the ejection aperture 52 in the lower surface of the housing 14. At this time, the driver 28 is in an initial, ready position above the holder 36. The ready position may be the position in which each base 30b of the driver 28 is positioned at a corner of the corresponding race 33 directly above a loaded holder 36 and the ejection aperture 52, where that race 33 is substantially rectangular. Each race 33 is defined in the housing 14, as is the ejection aperture 52. Thus, each race 33 and the ejection aperture 52 may occupy fixed positions relative to one another. As a result, where each race 33 is substantially rectangular, each race 33 may be positioned such that one side of the race 33 that extends substantially vertically is substantially aligned with the holder 36 and with the ejection aperture 52. Alternately, the ready position may be any suitable position within each race 33, particularly where the races 33 are curved or otherwise shaped.

The user actuates the surgical stapling tool 2 after the stapler head 8 has reached the desired position such that a cable or other force transmission member 12 moves the slider 16 proximally. Each base 30b of the driver 28 is positioned within the corresponding slot 22. The slot 22 may be shaped substantially as described above, or may be shaped differently. At least one base 30b of a post 30 of the driver 28 is sized to fit into and follow the slot 22 as the slider 16 moves. As the first portion 23 of the slot 22 is pulled proximally, the first portion 23 urges the corresponding base 30b downward in the corresponding groove 32, thus urging the driver 28 downward. The slots 22 are shaped such that the base 30b is initially moved substantially vertically a short distance such that the dog 30a corresponding to each base 30b moves downward a small amount into the vertical portion of the race 33. In the vertical portion of the race 33, the groove 32 is sized to be slightly wider than the dog 30a, such that the dog 30a is substantially restrained against horizontal movement. As the driver 28 moves downward, it contacts the base 40 of the staple 38 that is located in the holder 36 in firing position. The base 40 and the staple 38 may be substantially as described above. As the driver 28 continues to move downward, it pushes the staple 38 within the holder 36 toward the ejection aperture 52. The staple 38 may be deployed and released substantially as described above.

After deployment and release of the staple 38, tension on the force transmission member 12 is released. As a result, the force transmission member 12 exerts no force or a reduced force in the proximal direction on the slider 16. The biasing element 56 exerts a distal force on the slider 16, moving it distally toward its initial position. Alternately, the force transmission member 12 is substantially rigid and is moved distally after deployment and release of the staple 38, and the biasing element 56 is omitted. As the slider 16 moves distally, each dog 30a moves substantially proximally in the corresponding race 33, or remains substantially stationary as the slider 16 moves distally. The slots 22 are shaped such that the base 30b is initially moved substantially horizontally a short distance such that the dog 30a corresponding to each base 30b enters the horizontal portion of the race 33. In the horizontal portion of the race 33, the groove 32 is sized to be slightly taller than the dog 30a, such that the dog 30a is substantially restrained against vertical movement.

The driver 28 is configured to index the holders 36 proximally as the dog 30a moves relative to the horizontal portion of the race 33. Such indexing may be performed in any suitable manner. As one example, each holder 36 may include one or more pins or other members (not shown), each of which is configured to engage a corresponding opening 76 in the lower surface of the driver 28. When at least one pin or other member engages the corresponding opening 76, motion of the dog 30a (which is fixed to the driver 28) relative to the slider 16 causes relative motion of the holders 36 and the slider 16. As described above, the holders 36 may be connected or fabricated as a unitary cartridge. Thus, proximal motion of the dog 30a relative to the slider 16 and/or distal motion of the slider 16 relative to the dog 30a exerts a force in the proximal direction on the holders 36. As a result, this force pulls the detents 70 of the holders 36 out of the corresponding receivers 72 in the slider 16, causing the holders 36 to index proximally until each receiver 72 moves into the adjacent corresponding receiver 72. The distance between receivers 72 is substantially equal to the length of the horizontal groove 32 of the race 33, such that the driver 28 indexes the holders 36 a suitable distance. In this way, the detents 70 and corresponding receivers 72 act as the indexing mechanism 58. The ledge 74 restrains the holders 36 to substantially linear movement in response to the proximal force exerted by the driver 28 on the holders 36.

After further distal motion of the slider 16 and/or proximal motion of the dogs 30a, each dog 30a is positioned at a corner of the race 33, such that each dog 30a cannot move further proximally relative to the race 33. At this point, the slots 22 of the slider 16 urge the corresponding bases 30b of the posts 30 upward. As a result, the dogs 30a move upward along a vertical portion of the race 33. This vertical motion continues until each dog 30a encounters the upper proximal corner of the race 33. At this point, each base 30b may be positioned substantially at the proximal end of the corresponding slot 22 of the slider 16. As a result, further distal motion of the slider 16 pushes the bases 30b distally, thereby moving each dog 30a distally in the upper horizontal groove 32 of the race 33. The slider 16 is controlled to cease distal motion substantially at the time when each dog 30a arrives at the starting point on the race 33, which is the upper distal corner of the race 33, substantially above the ejection aperture 52 and a holder 36. The slider 16 may be controlled, for example, by providing a hard stop against the housing 14 or other portion of the stapler head 8 when the slider 16 has reached the point at which it has moved the dogs 30a to their starting points, by controlling the force transmission member or members 12, or in any other suitable manner.

Thus, in use the driver 28 is movable in two dimensions through the race 33. That is, the driver 28 moves both vertically and horizontally in response to actuation of the trigger 10. The driver 28 returns to its original starting position after reciprocating through two dimensions. The race 33 provides two degrees of freedom for the motion of the driver 28. In this way, the driver 28 may both deploy a staple 38 or other connector, and index the holders 36 after each deployment such that a new staple 38 or other connector is in place for deployment at the end of each actuation of the stapler head 8, unless all of the staples 38 or other connectors have been deployed from the stapler head 8.

Next, the stabilizer 37 is moved from the second position to the first position, freeing the stapler head 8 to move relative to the aorta 62. Such movement may be performed in any suitable manner, such as by performing actions that are substantially the opposite of those actions performed to move the stabilizer 37 from the first position to the second position. As one example, the stabilizer 37 may be biased to the first position, and tension may be released on the force transmission member holding the stabilizer 37 in the second position such that the biasing force on the stabilizer 37 returns it to the first position. As another example, the stabilizer 37 may be deflated. A number of staples 38 may need to be placed to secure the AAA graft 60 to the aorta 62. The handle 4 may be rotated and/or moved longitudinally along the aorta 62 to position the stapler head 8 in a different position for deploying another staple 38. Such motion of the handle 4 causes motion of the catheter 6, which in turn causes motion of the stapler head 8. Alternately, a rotary mechanism (not shown) in the handle 4 is used to rotate the stapler head 8 without having to rotate the entire handle 4. The stapler head 8 may be moved into each femoral artery 64 in proximity to the lower portion of the AAA graft 60 to staple that portion of the AAA graft 60 to the tissue of the femoral artery 64. The femoral artery 64 other than that in which the incision 65 is made may be accessed by steering the stapler head 8 via the catheter 6 using any standard catheter guidance method. Alternately, an incision is made in the other femoral artery 64, and the stapler head 8 is inserted through that incision to staple the AAA graft 60 to that femoral artery 64 and complete the procedure. Although the operation of the surgical stapling tool 2 has been described in the context of performing an AAA grafting procedure, the use and operation of the surgical stapling tool 2 is not limited to such a procedure. The surgical stapling tool may be used at any portion of the vasculature, of the interior of the heart, or any portion of the body that may be reached from the vasculature. Indeed, the surgical stapling tool 2 may be used to perform any suitable surgical procedure outside the vasculature, in a minimally invasive context or otherwise.

In the course of operation of the surgical stapling tool, the force transmission member 12 and other force transmission members may be manipulated as described above by any suitable mechanism or mechanisms. Thus, the particular configuration of the handle 4 is not critical, because it may be configured in any manner that controls the force transmission members as described above. As one example, the handle 4 may include a fluid-driven actuator that utilizes a working fluid such as compressed gas to drive one or more pistons in response to the actuation of the trigger 10; the force transmission member 12 may be coupled to one of those pistons, as may one or more other force transmission members. In this way, motion of the pistons causes motion of the corresponding force transmission member 12. Such a fluid-driven actuator is described in U.S. patent application Ser. No. 11/054,265 filed on Feb. 9, 2005, entitled "Anastomosis Tool Actuated with Stored Energy," which is hereby incorporated by reference in its entirety. Alternately, the handle 4 may include any other mechanism or mechanisms that manipulate the force transmission members 12 as described above after actuation of the trigger 10.

While the invention has been described in detail, it will be apparent to one skilled in the art that various changes and modifications can be made and equivalents employed, without departing from the present invention. It is to be understood that the invention is not limited to the details of construction, the arrangements of components and/or the details of operation set forth in the above description or illustrated in the drawings. Headings and subheadings are for the convenience of the reader only. They should not and cannot be construed to have any substantive significance, meaning or interpretation, and should not and cannot be deemed to be limiting in any way, or indicate that all of the information relating to any particular topic is to be found under or limited to any particular heading or subheading. The contents of each section of this document are merely exemplary and do not limit the scope of the invention or the interpretation of the claims. Therefore, the invention is not to be restricted or limited except in accordance with the following claims and their legal equivalents.

What is claimed is:

1. A method for stapling tissue, comprising:
   providing a surgical stapling tool including
      a stapler head,
      a plurality of staples generally parallel to and lying in different planes from each other, at least one of which is in a firing position,
      a plurality of holders, each said holder holding one of said staples, and
      a driver movable within said stapler head;
   placing said stapler head at a location in proximity to tissue; and
   actuating said driver to move in two dimensions, said actuating deploying at least one said staple into tissue from said firing position and indexing at least one of the remainder of staples into said firing position, wherein said indexing includes indexing said holders.

2. The method of claim 1, wherein said placing includes placing said stapler head at an intravascular location.

3. The method of claim 2, wherein said actuating is performed while fluid passes through the intravascular location.

4. The method of claim 1, wherein said surgical stapling tool includes a handle; wherein said actuating is performed in response to a single user input to said handle.

5. The method of claim 1, wherein said stapler head includes a stabilizer; further comprising moving said stabilizer to a position in contact with tissue before said actuating.

6. The method of claim 1, wherein each said holder includes at least one detent, and wherein said stapler head includes a plurality of receivers defined therein, each said receiver configured to receive a corresponding said detent; and wherein said indexing includes moving each said holder such that each detent thereof moves from engagement with one receiver into engagement with an adjacent receiver.

* * * * *